United States Patent
Kirsch et al.

(10) Patent No.: US 8,256,613 B2
(45) Date of Patent: Sep. 4, 2012

(54) SUTURE PACKAGING FOR BARBED SUTURES

(75) Inventors: David Kirsch, Madison, CT (US); Michael Prescott, Hamden, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 133 days.

(21) Appl. No.: 12/408,134

(22) Filed: Mar. 20, 2009

(65) Prior Publication Data

US 2009/0250356 A1 Oct. 8, 2009

Related U.S. Application Data

(60) Provisional application No. 61/031,040, filed on Apr. 7, 2008.

(51) Int. Cl.
*B65D 85/24* (2006.01)

(52) U.S. Cl. ....... 206/339; 206/380; 206/63.3; 242/170; 242/172

(58) Field of Classification Search ............... 206/63.3, 206/339, 380, 388, 392; 242/166, 172
See application file for complete search history.

(56) References Cited

U.S. PATENT DOCUMENTS

| | | | |
|---|---|---|---|
| 3,444,994 A | 5/1969 | Albert et al. | |
| 3,545,608 A | 12/1970 | Berger et al. | |
| 3,749,238 A | 7/1973 | Taylor | |
| 3,972,418 A | 8/1976 | Schuler et al. | |
| 4,424,898 A | 1/1984 | Thyen et al. | |
| 4,961,498 A | 10/1990 | Kalinski et al. | |
| 5,051,272 A | * 9/1991 | Hermes et al. | ............... 604/304 |
| 5,052,551 A | 10/1991 | Cerwin et al. | |
| 5,056,658 A | 10/1991 | Sobel et al. | |
| 5,154,283 A | 10/1992 | Brown | |

(Continued)

FOREIGN PATENT DOCUMENTS

DE 8800489 U1 4/1988
(Continued)

OTHER PUBLICATIONS

European Search Report for EP 09251050.2-2310 date of completion is Nov. 13, 2009 (3 pages).

(Continued)

*Primary Examiner* — David Fidei
*Assistant Examiner* — Raven Collins (57) ABSTRACT

The preset disclosure describes packaging for sutures having barbs. The packaging includes a base, a cover configured to be placed adjacent to the base to form the suture package and a plurality of protrusions which are configured for selectively maintaining and slideably releasing surgical barbed sutures. Additionally disclosed is a barbed suture package including a substantially flat base member having a top side, a bottom side, and an outer periphery, an outer wall extending upwardly from said top side of said base member about the periphery of said base member, said outer wall having a top, an outer surface, and an inner surface, at least one groove in said base member for receiving a suture, each of said grooves having an opening in a bottom and both sides and an opening in said top side of said base member, a needle park for receiving a needle, said needle park centrally mounted to said top side of said base member within the interior wall, and, a flat cover member having a top, a bottom, a suture discharge opening, and an outer periphery, wherein said cover member is mounted on said top of said outer wall.

13 Claims, 7 Drawing Sheets

U.S. PATENT DOCUMENTS

| | | | |
|---|---|---|---|
| 5,165,217 A | 11/1992 | Sobel et al. | |
| 5,179,818 A | 1/1993 | Kalinski et al. | |
| 5,186,972 A | 2/1993 | Williams et al. | |
| 5,213,210 A | 5/1993 | Cascio et al. | |
| 5,228,565 A | 7/1993 | Sinn | |
| 5,230,424 A | 7/1993 | Alpern et al. | |
| 5,236,083 A | 8/1993 | Sobel et al. | |
| 5,249,673 A | 10/1993 | Sinn | |
| 5,350,060 A | 9/1994 | Alpern et al. | |
| 5,359,831 A | 11/1994 | Brown et al. | |
| 5,372,251 A | 12/1994 | Thompson | |
| 5,462,162 A | 10/1995 | Kaplan et al. | |
| 5,472,081 A | 12/1995 | Kilgrow et al. | |
| 5,628,395 A | 5/1997 | Daniele et al. | |
| 5,655,652 A | 8/1997 | Sobel et al. | |
| 5,704,469 A * | 1/1998 | Daniele et al. | 206/63.3 |
| 5,833,055 A | 11/1998 | Cerwin et al. | |
| 5,906,273 A | 5/1999 | Pohle et al. | |
| 6,047,815 A | 4/2000 | Cerwin et al. | |
| 6,105,339 A | 8/2000 | Pohle et al. | |
| 6,135,272 A | 10/2000 | Sobel et al. | |
| 6,260,699 B1 | 7/2001 | Kaplan et al. | |
| 6,463,719 B2 | 10/2002 | Dey et al. | |
| 6,464,071 B2 | 10/2002 | Baumgartner | |
| 6,481,568 B1 | 11/2002 | Cerwin et al. | |
| 6,533,112 B2 | 3/2003 | Warnecke | |
| 6,804,937 B2 | 10/2004 | Dey et al. | |
| 2001/0000263 A1 | 4/2001 | Baumgartner | |
| 2003/0010655 A1 | 1/2003 | Alpern | |
| 2004/0050721 A1 | 3/2004 | Roby et al. | |
| 2005/0035007 A1 * | 2/2005 | Kennedy et al. | 206/63.3 |
| 2006/0226031 A1 | 10/2006 | Kennedy et al. | |
| 2007/0005110 A1 * | 1/2007 | Collier et al. | 606/228 |
| 2007/0227914 A1 | 10/2007 | Cerwin et al. | |
| 2007/0256945 A1 | 11/2007 | Kennedy et al. | |
| 2008/0185752 A1 | 8/2008 | Cerwin et al. | |

FOREIGN PATENT DOCUMENTS

| | | | |
|---|---|---|---|
| EP | 0356211 A2 | 2/1990 | |
| EP | 0471441 A | 2/1992 | |
| EP | 0931511 A | 7/1999 | |

OTHER PUBLICATIONS

European Search Report for EP 11000491.8-2310 date of completion is Mar. 17, 2011 (3 pages).

* cited by examiner

SUTURE PACKAGING FOR BARBED SUTURES

CROSS-REFERENCE TO RELATED APPLICATION

The present application claims priority to, and the benefit of, U.S. Provisional Patent Application Ser. No. 61/031,040, filed on Apr. 7, 2008, the entire contents of which are hereby incorporated by reference.

BACKGROUND

1. Technical Field

The present disclosure relates to packages for retaining surgical sutures, and more particularly to packages for selectively retaining and slideably releasing barbed surgical sutures.

2. Discussion of Related Art

A common form of surgical suture package is made of a folded stiff treated paper suture holder contained in a sterile, hermetically sealed envelope. This envelope is further sealed in a second, usually clear, although may be composed of foil, thermoplastic heat-sealed outer pouch to maintain the sterility of suture holder and inner envelope. When the suture is to be used, the outer pouch is opened, typically in the operating room, and the sealed sterile inner envelope is placed in a sterile area. Operating room personnel then open the inner envelope when access to the suture is needed.

Packages for surgical sutures having needles attached at one or both ends are constructed according to the suture material and to how the sutures will be used. Generally, the package holds the suture and attached needles in place, protects them during handling and storage, and allows ready access to the suture for removal with minimum handling.

An important aspect of the design and manufacture of suture packages is that the suture should be removable without becoming entangled with itself, kinked, coiled or bound in undesired ways. The nature of suture material itself may impose limitations on the configuration of the package, how the suture is placed within the package, the placement of the needles, or how the suture is drawn from the package. Barbed sutures impose a limitation on the configuration of the package.

Exemplary packaging for traditional surgical suture material is disclosed in U.S. Pat. No. 5,704,469 and U.S. Patent Application Publication No. 2006/0226031, the contents of which are incorporated herein by reference in their entirety. Both references disclose suture packaging configured for maintaining and releasing traditional surgical sutures. Generally, disclosed are suture packages including a base and a cover or lid formed of a rigid material. The base is configured to include a spiral channel or retaining portion for retaining a traditional surgical suture therein. The channel or retaining portion is typically top loaded and is configured for slideably releasing a suture as it is withdrawn from one end thereof.

Barbed sutures, unlike traditional surgical sutures, include barbs that must be accommodated within the suture packaging. Therefore, packaging for traditional surgical sutures may not be suitable packaging for barbed sutures. Specifically, any corners or edges in the packaging may cause the barbs of the suture to snag or otherwise lodge within the packaging. Additionally, and as will be described below, the cross-sectional profile of a traditional surgical suture differs from that of a barbed suture. Thus, packaging configured to retain a traditional surgical suture having a uniform cross-sectional profile is not readily used to retain a barbed suture having a varying cross-sectional profile.

A barbed suture may have any number of cross-sectional profiles depending on the size and radial spacing of the barbs about the suture. As will be described herein, and as shown in the figures, the barbed suture will include a cross-sectional profile defining at least two laterally spaced barbs. The aspects of the present disclosure should not, however, be limited to a barbed suture of a single configuration. It is envisioned that the barbs may be radially disposed about the barbed suture in any manner and may be configured with any lateral spacing. The lateral spacing between barbs may be uniform or random. It is further envisioned that the barbs may be of any size and of any configuration. Needles of various size and configuration may be operably engaged with one or both ends of the barbed suture.

When removed from packaging, if a barb is inadvertently snagged on a corner or edged, the barb may snap or otherwise bend, rendering at least that portion of the suture no more effective than a traditional surgical suture. A barbed suture may also be rendered less effective if a disproportionate number of the barbs become compressed or flattened. Thus, simply forcing a barbed suture into packaging configured for traditional surgical sutures may not only inhibit the ready removal of the suture from the package, it may also cause the compression or flattening of the barbs resulting in reduced effectiveness of the barbed suture.

The ability to readily access a barbed suture and efficiently retrieve the suture from its packaging is important, especially when time is of the essence during a surgical procedure. Thus, a continuing need exists for improved suture packages which significantly reduce the possibility of the barbed suture becoming entangled or caught within the suture package.

SUMMARY

Accordingly, the present disclosure provides novel methods and apparatus for surgical suture packaging that eliminate many problems associated with the prior art suture packages used for barbed sutures.

A surgical barbed suture package is disclosed. The package comprises a base and a cover configured to be placed adjacent to said base to form a suture package. The cover defines an opening therein to provide access to at least one needle and barbed suture contained within the package. The package includes an outer wall extending from an outer circumference of the base. The outer wall has a predetermined height such that the outer wall meets the cover when the cover is placed adjacent to the base. The outer wall defines an outer periphery of a suture retainer area. A plurality of protrusions positioned adjacent the outer wall extend inwardly toward the center portion of the package configured for supporting the surgical barbed suture.

The suture package further includes a platform having a peripheral wall for at least partially defining an inner periphery of the suture retainer area. Also included are a plurality of posts extending from the first and second arcuate end portions of a lower surface of the cover to define an inner periphery of arcuate end portions of the suture retainer area. The plurality of protrusions may form a continuous groove configured for selectively retaining and slidably releasing said barbed suture. At least two of said plurality of posts may be joined by webbing. The posts may be dimensioned and configured to engage holes formed in the base to secure the cover of the base.

The plurality of protrusions may define openings therebetween which are configured for slideably receiving the barbs of a barbed suture. The openings may be coated with a deformable plastic, polymer or the like. The coating may instead comprise a substantially gelatinous material.

Further disclosed is a surgical barbed suture package. The package comprises a base, a cover configured to be placed adjacent to said base to form said suture package, an outer wall extending from an outer circumference of the base, and a suture retaining area defined within said package. The outer wall has a predetermined height such that the outer wall meets the cover when the cover is placed adjacent the base. The suture retaining area extends from a bottom surface of the cover and has a height which is substantially equivalent to the height of the outer wall. The suture retaining area is configured for selectively retaining and slideably releasing a surgical barbed suture in an initial or uncompressed condition. A barbed suture is received within suture retaining area.

The suture package further includes a needle park for maintaining a needle in a fixed position. The needle is connected to an end of a suture which is positioned within the suture retaining area. The needle park is located on an upper surface of the cover. The needle park is located on the upper surface of the base. The suture retaining area comprises at least one protrusion extending from a lower surface of the cover. The surgical barbed suture is wound within the suture retaining area A needle is attached to an end of said barbed suture is positioned within a central region of the base, as defined by the suture retaining area, such that the needle engages a needle park to maintain the needle in a fixed position. The suture retaining area comprises a wall extending from a lower surface of said cover. The barbed suture is wound within the suture retaining area beginning in a portion of the suture-retaining area adjacent to the outer wall. The cover has a circumference dimension which is substantially equal to a circumference dimension of said base.

The suture retaining area defined within the suture package comprises a plurality of sets of protrusions extending from a lower surface of the cover. The suture package further includes posts formed on ends of the protrusions. The posts are dimensioned and configured to engage holes formed in the base to secure the cover to the base.

Also disclosed is a suture package, comprising a substantially flat base member, a needle park for receiving a needle, and a flat cover member. The base member includes a top, a bottom, a suture discharge opening, and an outer periphery having a top side. The flat cover member includes a bottom side, and an outer periphery, an outer wall extending upwardly from the top side of the base member about the periphery of the base member. The needle park is centrally mounted to the top side of the base member within the interior wall. The cover member is mounted on the top of the outer wall. The outer wall includes a top, an outer surface, and an inner surface. At least one groove is formed in said base member for receiving a suture. Each of the grooves defines an opening in the top side of the base member. The suture package additionally includes a surgical needle and barbed suture.

Additionally, disclosed is a barbed suture package. The package comprises a base defining at least one spiral track, a cover configured to overlie the base, and support structure disposed in the spiral track for supporting a barbed suture in an uncompressed state. The cover defines an opening in communication with the spiral track. The support structure includes a plurality of wires suspended across the spiral track.

The barbed suture package further includes a barbed suture. The barbed suture includes at least one needle thereon. The package is configured to include at least one needle park for receiving the at least one needle. The barbed suture package may include a double armed folded suture.

The spiral track of the barbed suture package include a coating for assisting in maintaining one or more barbed sutures in an uncompressed state. The spiral track may further include a coating for assisting in removal of one or more barbed suture. The barbed suture package may further include a label for identifying the contents thereof.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION THE DRAWINGS

Embodiments of the presently disclosed suture package will now be described in detail with reference to the figures, in which like reference numerals identify corresponding elements throughout the several views.

Figure 1:
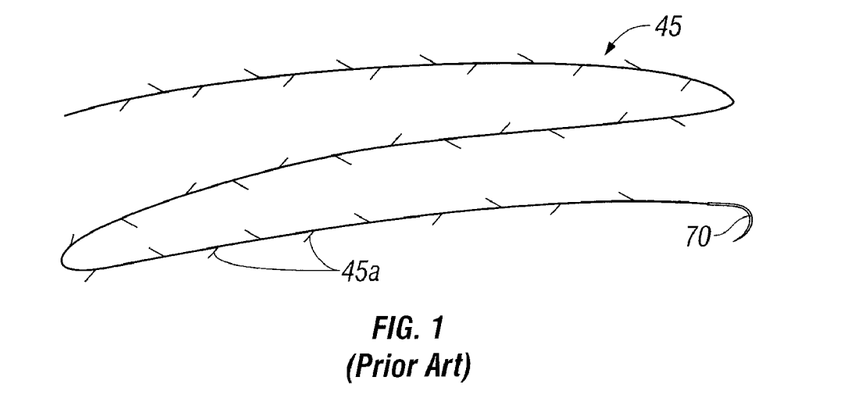
FIG. 1 is a perspective view of a barbed suture including a needle on one end thereof.
Figure 2A:
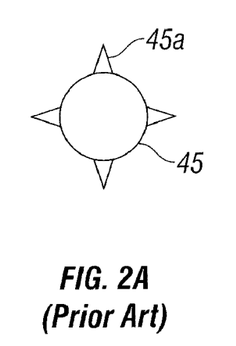
FIGS. 2A-2C are cross-sectional end views of various barbed sutures have different barb configurations.
Figure 2B:
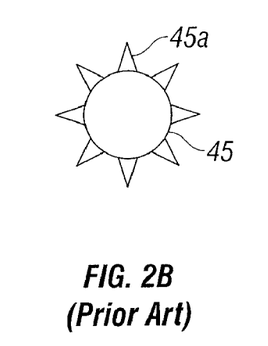
Figure 2C:
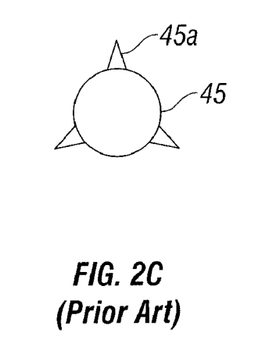

Unless otherwise specified, any further reference to sutures should be understood to refer to sutures having barbs. FIG. 1 illustrates a first embodiment of a barbed suture 45 as will be discussed herein. Barbed suture 45 includes a needle 70 disposed on a first end thereof. Needle 70 may be of any size or configuration. Needle 70 may further be configured for selectively releasable engagement with barbed suture 45. Barbed suture 45 further comprises barbs 45a. Barbs 45a may be of any size or configuration. Furthermore, barbed suture 45 may have various cross-sectional profiles (FIGS. 2A-2C). From this point forth, any references to barbed suture 45 will be with regards to a barbed suture defining a substantially cross-shaped cross-sectional profile (FIG. 2A). However, it is envisioned that the aspects of the present disclosure may be modified to accommodate barbed sutures of any size and cross-sectional profile.

Figure 3:
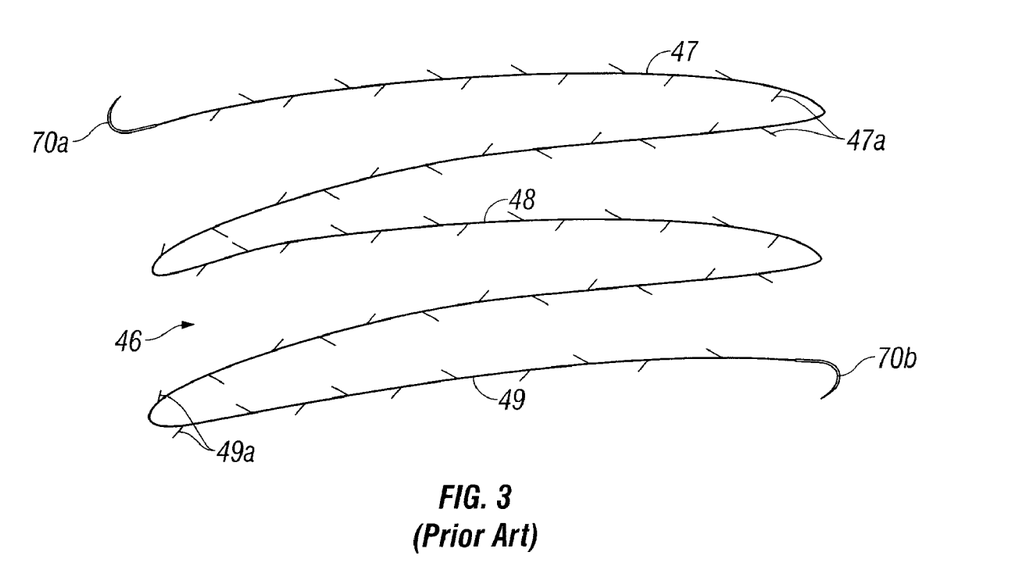
FIG. 3 is a perspective view of a barbed suture including a needle on both ends thereof.

Turning to FIG. 3, in an alternate embodiment of a barbed suture, barbed suture 46 includes a first needle 70a disposed on a first end thereof and a second needle 70b disposed on a second end thereof. Barbed suture 46 defines a first section 47 defining barbs 47a along the length thereof, extending away first needle 70a, a second section 49 defining barbs 49a along the length thereof, extending away from second needle 70b and a transition zone 48 therebetween. In this manner, when barbed suture 46 is grasped at transition zone 48 and needles 70a, 70b are permitted to hang, barbs 47a, 49a extend in substantially the same direction. As with barbs 45a of barbed suture 45, barbs 47a, 49a of barbed suture 46 may define various cross-sectional profiles. Also, as with barbed suture 45, hereinafter, barbed suture 46 will be described with reference to a substantially cross-shaped cross-sectional profile (FIG. 2A). However, it is envisioned that the aspects of the present disclosure may be modified to accommodate double needled barbed sutures of any size and cross-sectional profile.

Figure 4:
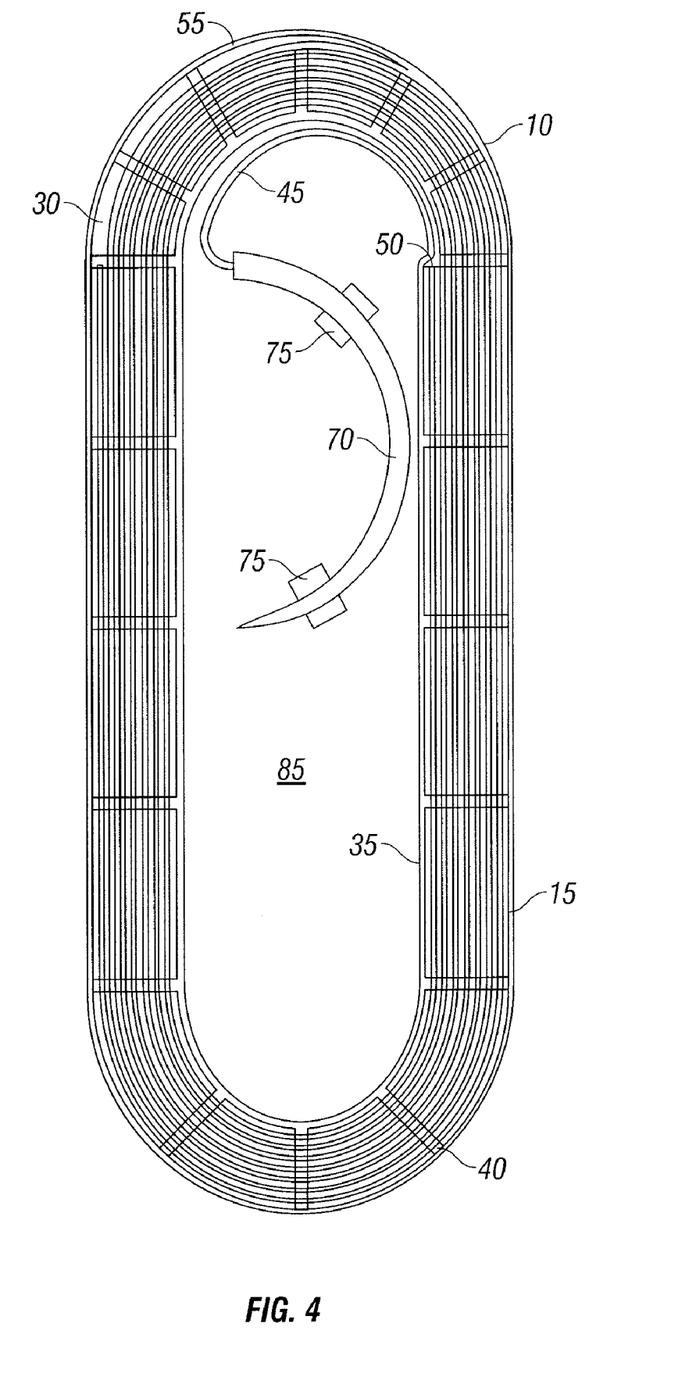
FIG. 4 is a top view of an embodiment of a suture package in accordance with an embodiment of the present disclosure.
Figure 5A:
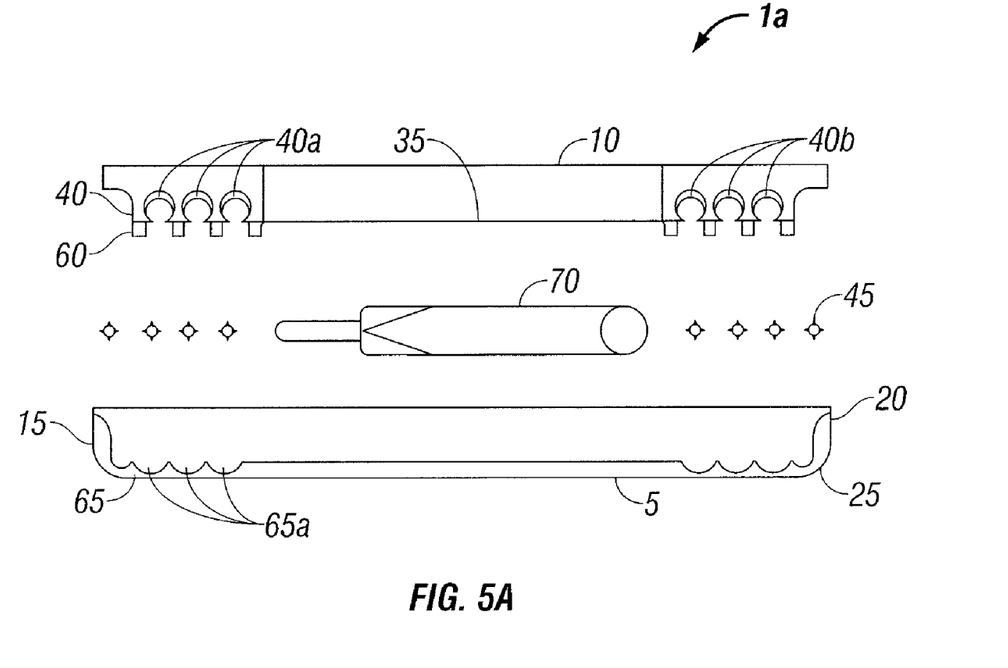
FIG. 5A is a side cross-sectional view of the suture package illustrated in FIG. 4 configured for holding a barbed suture having only a single needle.

Referring now to FIGS. 4 and 5A, there is shown a top view and a side cross-sectional view, respectively, of an embodiment of a suture package for maintaining and dispensing barbed sutures in accordance with an embodiment of the present disclosure. Suture package 1a includes a base 5 and a cover 10. An outside wall 15 rises from base 5 and extends like an oval around a circumference of base 5. Outside wall 15 has an upper rim 20 and a lower rim 25. Lower rim 25 is connected to base 5. Outside wall 15 is designed having a predetermined height such that upper rim 20 engages cover 10, preferably at the circumference thereof. Thus, when base 5 and cover 10 are moved adjacent each other, the outer circumference of cover 10 is joined with the upper rim 20 of outside wall 15 to form an outer wall of closed suture package 1.

A suture retaining area 30 is defined on an outer boundary by outside wall 15, and on an inner boundary by an inner or interior wall 35. In accordance with an embodiment of the present disclosure, interior wall 35 preferably extends downward from cover 10. Unlike outside wall 15, interior wall 35 is not a continuous loop. Instead, interior wall 35 has a first end and a second end which will be described in further detail below. Adjacent to the first end of interior wall 35, an opening is defined which allows a first end of a barbed suture 45 to enter into the suture retaining area 30. Interior wall 35 is also configured to follow the shape of the suture retaining area 30. Thus, at the point of the opening formed by interior wall 35, the end of interior wall 35 is offset from any other portion of interior wall 35. This offset helps to maintain the shape of suture retaining area 30 and to provide an opening for barbed suture 45 to access suture retaining area 30.

Alternatively, it is contemplated that interior wall 35 may define an outer boundary of a plateau region in the center of cover 10. The height of the plateau region (also referred to as suture-removal area 85) is configured to be equivalent to the height of suture retaining area protrusions 40 less the thickness of a needle 70. Accordingly, a needle 70 may be positioned on the plateau in suture-removal area 85, on the outside surface of cover 10. In the case wherein it is desired to park needle 70 on the exterior of suture package 1a, a spacer may be placed on the plateau in suture-removal area 85. In another embodiment, interior wall 35 defines an oval opening within cover 10. In that case, it is preferred that a needle park 75 is attached to base 5 within suture-removal area 85. Therefore, surgical personnel have the ability to access and remove needle 70 through the opening within cover 10.

Extending downward from cover 10 is structure that partitions suture package 1a into one or more suture retaining areas 30. More specifically, a plurality of sets of four suture retaining area protrusions 40 define a corresponding number of suture retaining areas 30. The sets of suture retaining area protrusions 40 are displaced radially from a center of the cover 10. It is also contemplated that the sets of suture retaining area protrusions 40 may be configured as more or less than four retaining area protrusions such that more or less suture retaining areas are defined. Additionally, it is contemplated that the suture retaining area protrusions 40 may be configured as one or more continuous walls forming a spiral groove for retaining barbed suture 45. Protrusions 40 are preferably radially aligned, however, it is envisioned that protrusions 40 may be staggeredly positioned within suture retaining area 30 to accommodate barbed sutures 45 of various configurations. Protrusions 40 may be positioned within cover 10 to correspond with the non-barbed sections of suture 45 as it is retained within suture package 1. By supporting barbed suture 45 in this manner, barbs 45a are prevented from being compressed or flattened under the weight of barbed suture 45 as it is inserted into and retained within suture package 1.

Suture retaining area protrusions 40 are elongated finger members having a height which is substantially equivalent to the height of outside wall 15. Suture retaining area protrusions 40 are connected on a first end to the bottom surface of cover 10. Suture retaining area protrusions 40 define suture retaining areas 30 on the bottom of cover 10. As shown, cover 10 includes a plurality of sets of four suture retaining area protrusions 40 extending radially outward between interior wall 35 and outside wall 15. Thus, suture retaining area 30 defines and provides for four revolutions of barbed suture 45. As discussed above, suture retaining area 30 may provide for more or less than four revolutions of barbed suture 45.

Protrusions 40 define openings 40a therebetween for selectively receiving and slideably releasing barbed suture 45. Openings 40a may define a circular cross-sectional profile sized to retain barbed suture 45 whereby barbs 45a are maintained in an uncompressed condition. Preferably, opening 40a includes a rounded surface and/or is coated to prevent snagging of barbed suture 45. Openings 40a may include a coating 40b that permits barbs 45a of barbed suture 45 to remain in an initial or uncompressed condition while maintained within opening 40a. Coating 40b may be a soft, highly deformable material, or may instead include a semi-liquid or gelatinous material. In either instance, barbs 45a of barbed suture 45 may be maintained within opening 40a while causing minimal compression of barbs 45a. Coating 40b may reduce the friction between barbed suture 45 and protrusions 40, thereby making for easier withdrawal of barbed suture 45 from within opening 40a. Coating 40b may remain within openings 40a as barbed suture 45 is withdrawn therefrom.

Alternatively, it is envisioned that coating 40b may include an antibiotic, healing agent or the like, and may remain on barbed suture 45 as it is removed from suture package 1a to increase the effectiveness of barbed suture 45.

A second end of suture retaining area protrusions 40 has a post 60 extending therefrom. Posts 60 are dimensioned to fit within holes 65 which are formed in base 5. Holes 65 may instead define dimples or recesses. Posts 60 may also be heat staked or otherwise welded to base 5 to secure the cover 10 to the base 5. Base 5 may further be configured to include a notch or groove 65a disposed between holes 65 and corresponding to openings 40a. As cover 10 is received within base 5, posts 60 extending from suture retaining area protrusions 40 engage holes 65 which are defined by base 5. In this manner, opening 40a and groove 65a are joined to form a cavity for receiving barbed suture 45. This arrangement provides structural support to the suture package. The ends of the protrusions 40 may, alternatively, be deformed in the manner of rivets after the cover 10 has been fitted onto the base 5 with the wall 15. Other and/or additional types of connection between the wall 15 and the cover 10 are possible. Thus, e.g., the use of catches, which project at the periphery of the cover 10 and engage suitable counterparts at wall 15, is contemplated.

A first end 50 of the suture retaining area 30 opens into a suture-removal area 85 which, in the embodiments illustrated in FIGS. 4 and 5A is arranged in the zone surrounded by the suture retaining area 30. The second end 55 of the suture retaining area 30 is closed (FIG. 4). The suture retaining area 30 is closed to the bottom by base 5.

A needle park assembly 75 is provided within the central section of the suture-removal area 5 on an outer surface of cover 10 or an inner surface of base 5. The structure of needle park assembly 75 is known to one having ordinary skill in the art. See, for example, U.S. Pat. Nos. 6,481,569, 5,788,062, 5,472,081, 5,180,053, 5,131,533, 5,099,994, and 4,424,898. It is contemplated that cover 10 includes an opening which permits free access to the suture-removal area 85. The opening may be a partial opening in the cover, or a more extensive opening, the advantages of each of which will be described below. Surgical personnel can gain access to the armed suture through the opening in cover 10 and remove armed suture by disengaging needle 70 from needle park assembly 75 and then pulling barbed suture 45 from suture retaining area 30. It is to be noted that needle 70 is positioned within the inner space defined by barbed suture 45. This configuration further assists in the removal of the armed suture from the package.

Figure 6A:
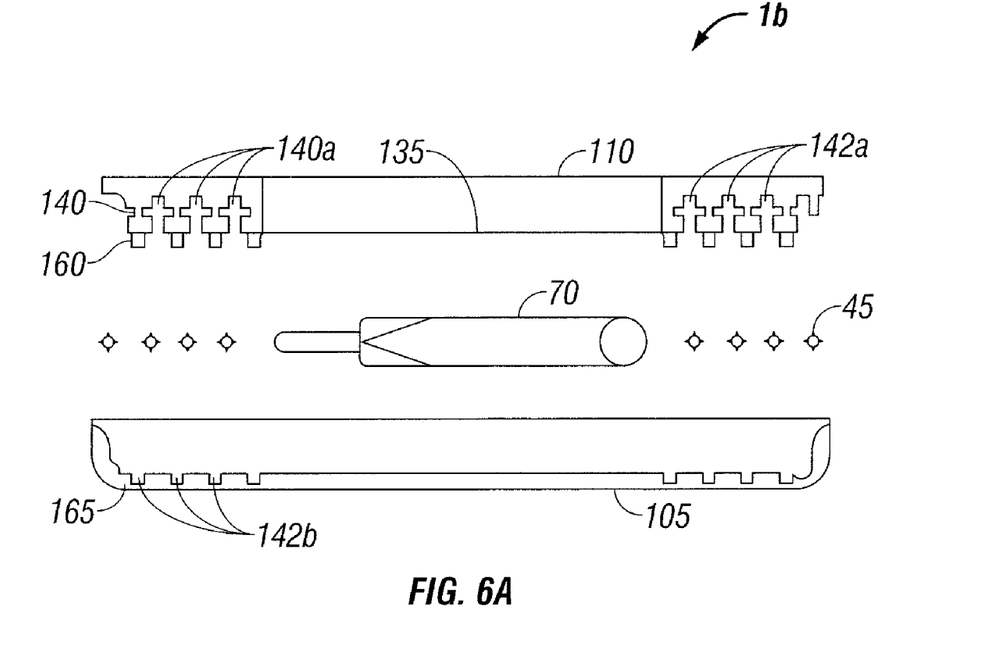
FIG. 6A is a side cross-sectional view of an alternate embodiment of the suture package of FIG. 4 configured for holding a barbed suture having a needle.

Turning now to FIG. 6A, in another embodiment of previously disclosed suture package 1 a, base 105 and cover 110 of suture package 1b are substantially as discussed above and will only be described in detail as relates to the difference therebetween. Base 105 and cover 110 define suture retaining area protrusion 140. Protrusions 140 form openings 140a for selectively retaining and slideably releasing barbed suture 45. Openings 140a include slots or grooves 142a configured to permit barbs 45a of barbed suture 45 to remain expanded therein as barbed suture is maintained in and slideably released from opening 140a. In addition to holes 165 formed in base 105 for receiving posts 160 formed on protrusions 140, base 105 further defines slots 142b. Slots 142b function in a similar manner to slots 142a, permitting barbs 45a of barbed suture 45 to remain uncompressed. As noted above and as discussed herein, barbed suture 45 defines a cross-shaped cross-sectional profile, thus slots 142a, 142b also define a cross-shaped cross-sectional profile for selectively maintaining and slideably releasing barbed suture 45.

Figure 5B:
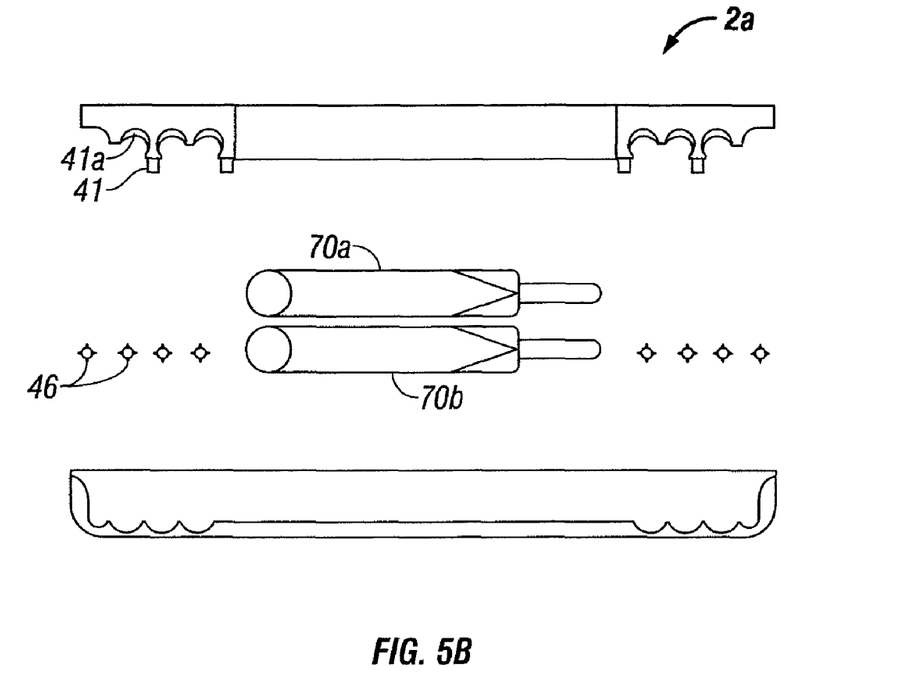
FIG. 5B is a side cross-sectional view of an alternate embodiment of the suture package illustrated in FIG. 4 configured for holding a barbed suture having a needle disposed on each end thereof.
Figure 6B:
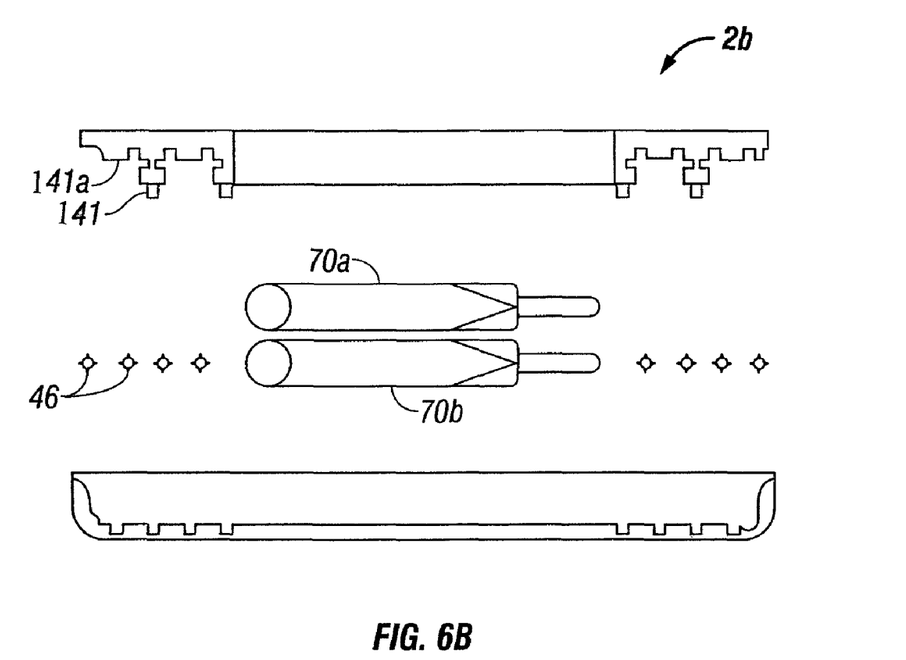
FIG. 6B is a side cross-sectional view of an alternate embodiment of the suture package of FIG. 4 configured for holding a barbed suture having a needle disposed on each end thereof.

With reference now to FIGS. 5B and 6B, suture packages 1a and 1b, as described above, may be modified to selectively maintain and slideably release double needled barbed suture 46. As discussed above, barbed suture 46 includes first and second needles 70a, 70b and corresponding first and second barbed sections 47, 49, respectively (FIG. 3). Unlike with barbed suture 45 where barbs 45a are aligned in the same direction, and thus, is capable of being retained in a single spiral track, barbed suture 46 includes barbed sections 47, 49 each having barbs 47a, 49a that extend in opposite directions, thereby eliminating possibility of using a single spiral track to retain barbed suture 46. However, as discussed above, when barbed suture 46 is grasped at transition zone 48 and needles 70a, 70b are extended together, barbs 47a, 49a of barbed sections 47, 49, respectively, aligned.

With reference still to FIGS. 5B and 6B, suture packages 2a, 2b are modified to selectively receive and slidably release barbed suture 46. Suture packages 2a, 2b are substantially similar to suture packages 1a, 1b (FIGS. 5A and 6A) hereinabove described. Suture packages 2a, 2b will be described as relates to the differences between suture packages 1a, 1b, respectively. In order to maintain first and second barbed sections 47, 49 adjacent one another and, thus, prevent entangling between barbs 47a, 49a during insertion into and removal from suture packages 2a, 2b, protrusions 41, 141, respectively, may form double wide openings 41a, 141a, respectively, for receiving barbed suture 46. In this manner, barbed suture 46 may be grasped at a transition zone 48 (FIG. 3) and folded such that first and second needles 70a, 70b are adjacent one another. Transition zone 48 is positioned between first and second barbed sections 47, 49 and may be located anywhere along the length of barbed suture 46. Barbed suture 46 may then be received within double wide openings 41a, 141a in a similar manner as described above for barbed suture 45 within suture packages 1a, 1b. Suture packages 2a, 2b may further be configured to include a needle park (not shown) for retaining first and second needles 70a, 70b.

Figure 7:
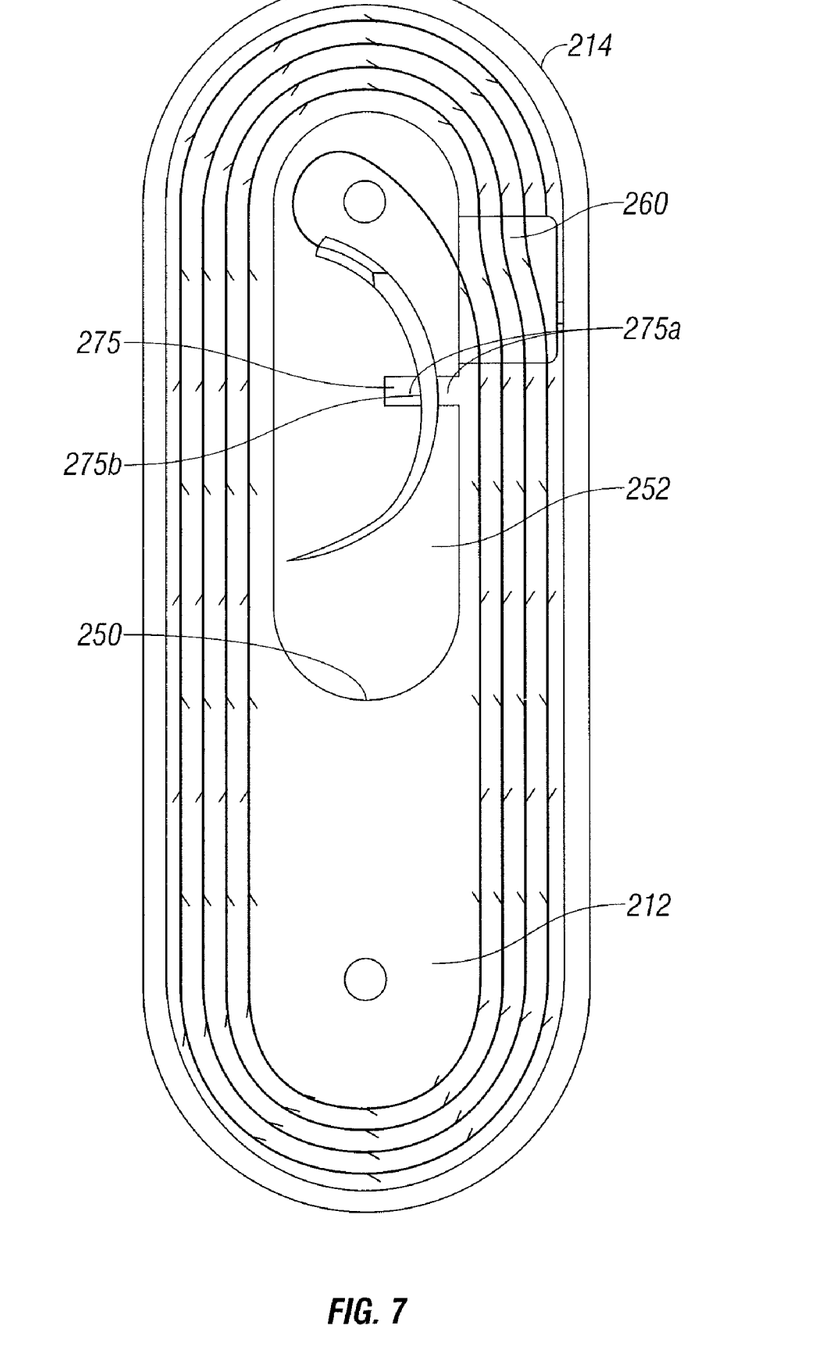
FIG. 7 is a top view of an another embodiment of a suture package in accordance with an embodiment of the present disclosure.
Figure 8A:
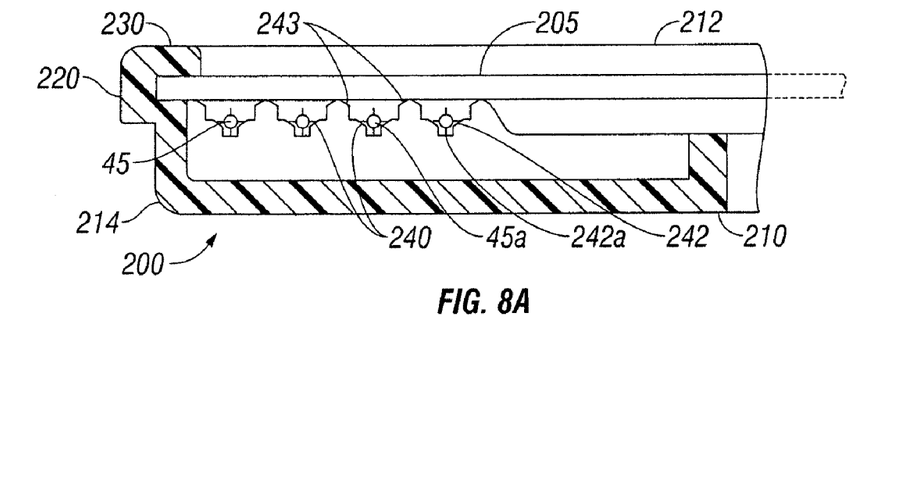
FIG. 8A is a side cross-sectional view of the suture package illustrated in FIG. 4, configured for holding a barbed suture having a single needle.

Referring now to FIGS. 7 and 8A, another embodiment of the package of the present disclosure is shown as suture package 200. Package 200 is seen to have flat, oval shaped base member 210. Base member 210 may have other configurations including circular, rectangular, square, combinations thereof and the like. Base member 210 defines pin openings 215 therethrough. Base member 210 includes top 212 and outer periphery 214. Extending upwardly from the top 212 of the periphery 214 of base member 210 is the outer wall 220. Outer wall 220 includes inner surface 221 and top 222. Extending from the top 222 of outer wall 220 is the closure lip 230. Grooves 240 extend into top 212 of base member 210. The grooves 240 may be concentric. The grooves 240 begin and end on either side of the optional crossover indentation 260. The crossover indentation is a cavity extending into the top of the base member 210. The grooves 240 form the suture-winding channel 250.

Grooves 240 include a top opening 241, bottoms 242 and sides 243. Referring particularly to FIG. 8A, bottoms 242 and sides 243 are configured to form slots 242a, 243a, respectively. Slots 242a, 243a extend the length of grooves 240. Slots 242a, 243a are configured to permit barbed suture 45 to be selectively received with and scoveringly release from suture package 200. In this manner, barbed suture 45 may be maintained within grooves 240 while barbs 45a thereof extend into slots 242a, 243a. Barbs 45a of barbed suture 45 may then be maintained in an uncompressed condition within suture package 200.

Interior to the grooves is a needle well 250 extending into a top 212 of base member 210. Well 250 is a cavity having bottom 272 for receiving surgical needle 70. Extending upwardly from the bottom 252 of the well 250 is the needle park 275. Needle park 275 includes a pair of opposed members 275a separated by an opening 275b. A surgical needle 70 is frictionally engaged in the opening 275b. A cover member 205 is mounted to outer wall 220 and retained in place by bonding over the closure lip 230 to engage the outer periphery of the cover 205.

Figure 9A:
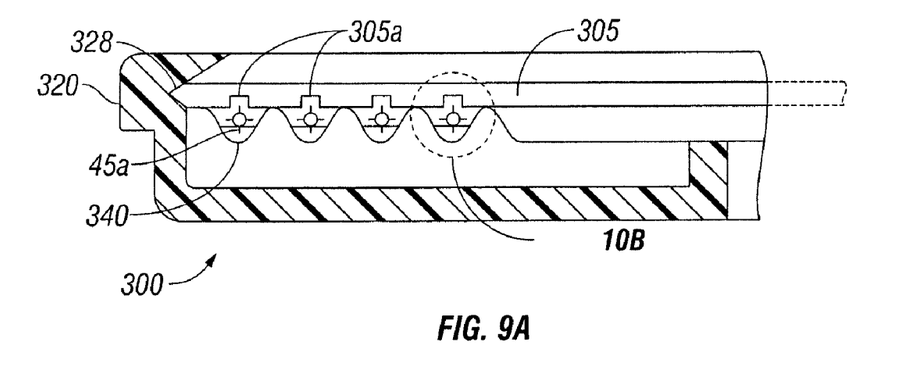
FIG. 9A is a side cross-sectional view of an alternate embodiment of the suture package of FIG. 7 configured for holding a barbed suture having a needle.

Referring now to FIG. 9A, yet another embodiment of a suture package is disclosed. Suture package 300 is substantially similar to suture package 200 and will only be described as relates to the differences therebetween. Unlike suture package 200 wherein grooves 240 defined by base member 210 included slots 242, 243 for retaining barbs 45a, suture package 300 includes cover 305 configured to include a slot 305a for receiving at least one row of laterally disposed barbs 45a. Cover 305 received within a retention groove 328 formed in the inner side of the outer wall 320. As cover 305 slides into position within groove 328 and over grooves 340, slot 305a defined in cover 305 receives at least a row of laterally disposed barbs 45a. In this manner, cover 305 may retain barbed suture 45 within groove 340 without compressing barbs 45a. Thus, barbs 45a are prevented from being flattened. Additionally, an uncompressed barbed suture 45 is more readily withdrawable from within suture package 300. As discussed above, groove 340 may be sized or dimensioned to selectively retain and slideably release barbed sutures of any configuration, and is not limited to barbed suture 45 having a cross-shaped cross-sectional profile.

Figure 10A:
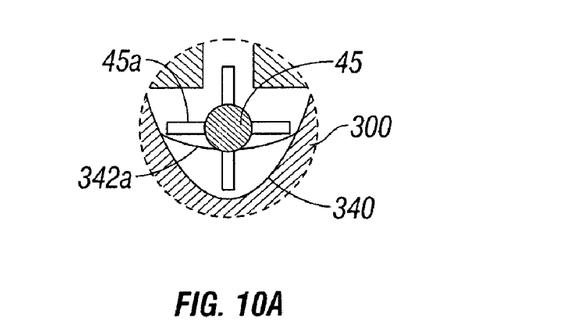
FIG. 10A is an enlarged view of portion 10 of FIG. 9A showing a first embodiment of a barbed suture support.
Figure 10B:
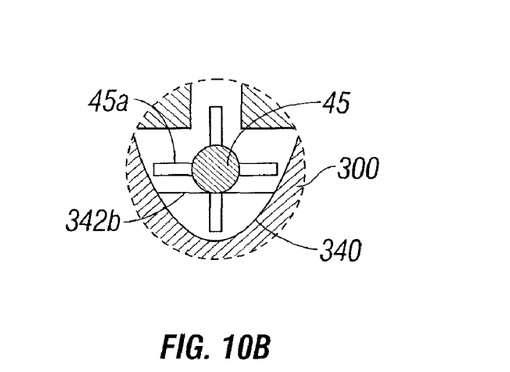
FIG. 10B is an enlarged view of portion 10 of FIG. 9A showing a second embodiment of a barbed suture support.

Referring now specifically to FIG. 10B, suture package 300 may further include supports 342b, extending across grooves 340 for maintaining barbed suture 45 in a supported position. Supports 342b may comprise wire or other material. Suture supports 342b may extend horizontally across groove 340 as shown in FIG. 10B. In other embodiments, as shown in FIG. 10A, suture supports 342b may instead form an angle. By maintaining barbed suture 45 in a supported position, supports 342b prevent compression or flattening of barbs 45a. Supports 342b may be spaced about groove 340 uniformly, to correspond with barbs 45a formed on barbed suture 45, or instead, supports 342b may be randomly spaced about groove 340. Supports 342b may be extremely thin. Supports 342b may be configured to separate from within groove 340 or break as suture 45 is removed from suture package 300. In this manner, barbed suture 45 may be more easily removed from with suture package 300.

Figure 8B:
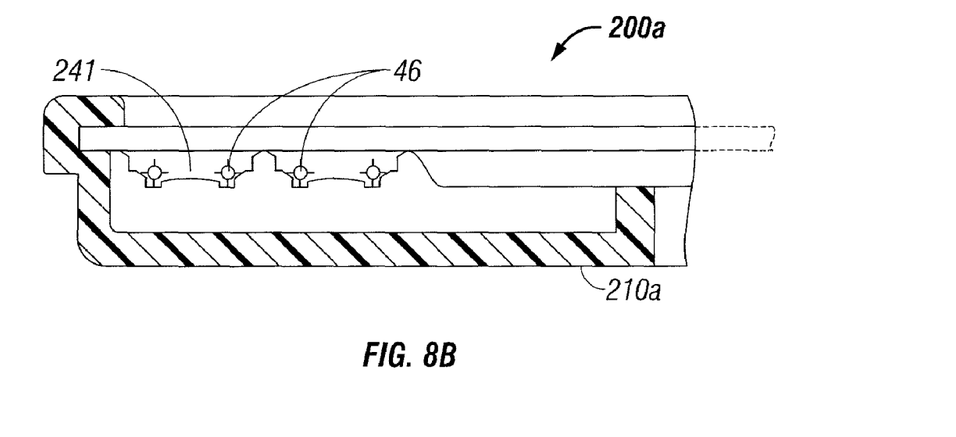
FIG. 8B is a side cross-sectional view of an alternate embodiment of the suture package illustrated in FIG. 7, configured for holding a barbed suture having a needle disposed on each end thereof.
Figure 9B:
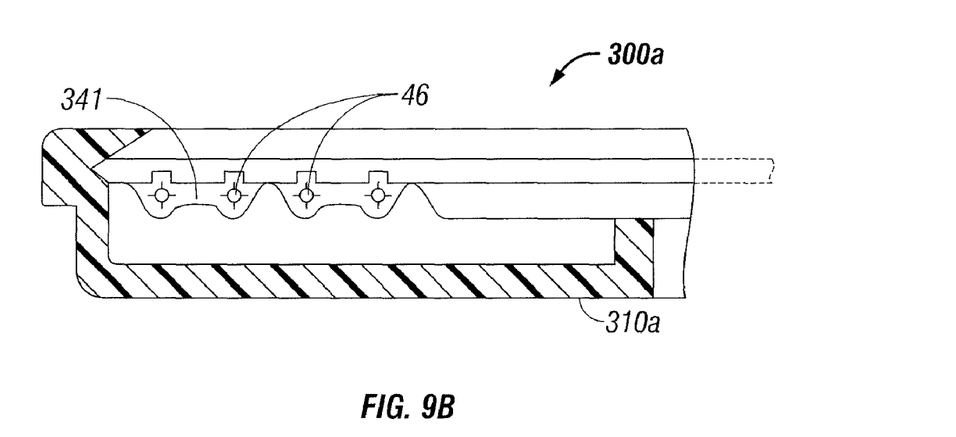
FIG. 9B is a side cross-sectional view of an alternate embodiment of the suture package of FIG. 7 configured for holding a barbed suture having a needle disposed on each end thereof.

Turning now to FIGS. 8B and 9B, suture packages 200a, 300a, are substantially similar to suture packages 200, 300, respectively, therefore, will only be described as relates to the differences therebetween. Suture packages 200, 300 may also be modified to selectively retain and slidably release double needled barbed suture 46. Bases 210a, 310a define double wide openings 241, 341 configured for retaining folded barbed suture 46. Barbed suture 46 may be selectively received within and slidably withdrawn from suture packages 200a, 300a in a similar manner as described above.

Any of the above suture packages may be configured to retain absorbable sutures. Absorbable sutures are subject to hydrolytic degradation, and therefore must be packaged in an airtight sealed container which is substantially impervious to water. Typical air-tight packaging includes a laminate film having a metallic foil layer. One known method of "bone dry" packaging of absorbable sutures is described in U.S. Pat. No. 3,728,839 to Glick, the entire contents of which are incorporated herein by reference. In this method, the gaseous contents of the suture envelope are either evacuated or replaced with a gas which is inert towards the absorbable suture prior to sealing the packaging. As described in commonly owned U.S. Pat. No. 5,051,272, the entire contents of which are hereby incorporated by reference, a storage stabilizing mixture may be added to the suture packaging to assist in maintaining "bone dry" packaging. By adding the storage stabilizing mixture to the suture packaging any moisture that manages to enter the suture packaging is absorbed by the mixture and not the absorbable suture, thereby preventing the degradation of the absorbable suture.

It will be understood that various modifications may be made to the embodiments disclosed herein. For example, although the above embodiments are described with reference to a surgical suture package, it is contemplated that the disclosure is not limited to such an application and may be applied to various medical instruments. Additionally, although the illustrative embodiments described herein disclose a single needle-suture combination within the package, it is contemplated that multiple sutures may be housed within a single suture package. In another example, rather than mounting the needle park to a surface of the cover, the needle park can be located on a surface of the base. Also, rather than removing the suture-needle combination through an opening in the cover, it is contemplated that the suture-needle combination can be removed through an opening formed in the base. Therefore, the above description should not be construed as limiting, but merely as exemplifications of preferred embodiments. Those skilled in the art will envision other modifications within the scope and spirit of the claims.

What is claimed is:

1. A surgical barbed suture package comprising:
   a base;
   a cover configured to be placed adjacent to said base to form a suture package;
   an outer wall extending from an outer circumference of said base, said outer wall having a predetermined height such that said outer wall meets said cover when said cover is placed adjacent said base; and
   at least one suture retaining area within said package having a circular cross-section, wherein said area extends from a bottom surface of said cover and has a height which is substantially equivalent to the height of said outer wall, said suture retaining area selectively retaining and slideably releasing a surgical barbed suture in an initial or uncompressed condition and wherein said suture retaining area includes grooves defined in the top side of the base corresponding to the suture retaining area and configured to permit barbs of a barbed suture to extend therein.

2. The surgical barbed suture package of claim 1, wherein said suture package further includes a needle park for maintaining a needle in a fixed position, wherein said needle is connected to an end of a suture which is positioned within said suture retaining area.

3. The surgical barbed suture package of claim 2, wherein said needle park is located on an upper surface of said cover.

4. The surgical barbed suture package of claim 2, wherein said needle park is located on the upper surface of said base.

5. The surgical barbed suture package of claim 1, wherein the suture retaining area comprises at least one protrusion extending from a lower surface of said cover.

6. The surgical barbed suture package of claim 1, wherein a surgical barbed suture is positioned within said suture retaining area.

7. The surgical barbed suture package of claim 1, wherein a needle attached to an end of said barbed suture is positioned within a central region of said base, as defined by said suture retaining area, such that said needle engages a needle park to maintain said needle in a fixed position.

8. The surgical barbed suture package of claim 1, wherein the suture retaining area comprises a wall extending from a lower surface of said cover.

9. A surgical barbed suture package, comprising:

a substantially flat base member having a top side, a bottom side, and an outer periphery;

an outer wall extending upwardly from said top side of said base member about the periphery of said base member, said outer wall having a top, an outer surface, and an inner surface;

at least one groove in said base member for receiving a barbed suture in an uncompressed condition, each of said grooves having an opening in said top side of said base member, and including at least one support extending across the groove for maintaining a barbed suture in a supported position;

a needle park for receiving a needle, said needle park centrally mounted to said top side of said base member within the interior wall; and, a flat cover member having a top, a bottom, a suture discharge opening, and an outer periphery, wherein said cover member is mounted on said top of said outer wall.

10. The surgical barbed suture package of claim 9, additionally comprising a surgical needle and barbed suture.

11. The surgical barbed suture package of claim 1, wherein at least a portion of the suture retaining area is coated.

12. The surgical barbed suture package of claim 1, further including a storage stability mixture for absorbing moisture.

13. The surgical barbed suture package of claim 9, wherein the at least one support comprises a wire.

* * * * *